(12) United States Patent
Butenas et al.

(10) Patent No.: US 6,566,493 B1
(45) Date of Patent: May 20, 2003

(54) PEPTIDOMIMETICS CONTAINING 6-PEPTIDYLAMINO-1-NAPHTHALENESULFONAMIDE MOIETIES

(75) Inventors: Saulius Butenas, South Burlington, VT (US); Kenneth G. Mann, Grand Isle, VT (US)

(73) Assignee: The University of Vermont, Burlington, VT (US)

( * ) Notice: Subject to any disclaimer, the term of this patent is extended or adjusted under 35 U.S.C. 154(b) by 0 days.

(21) Appl. No.: 09/308,437

(22) PCT Filed: Nov. 18, 1997

(86) PCT No.: PCT/US97/21075

§ 371 (c)(1),
(2), (4) Date: Sep. 9, 1999

(87) PCT Pub. No.: WO98/22125

PCT Pub. Date: May 28, 1998

Related U.S. Application Data

(60) Provisional application No. 60/031,359, filed on Nov. 19, 1996.

(51) Int. Cl.[7] .................................................. C07K 7/02
(52) U.S. Cl. .......................... 530/329; 514/17; 514/18; 514/19; 514/2; 530/331; 530/345; 435/23
(58) Field of Search .............................. 514/17, 18, 19, 514/2; 530/331, 329, 345; 435/23

(56) References Cited

U.S. PATENT DOCUMENTS 5,399,487 A    3/1995    Buténas et al.    ............... 435/13

FOREIGN PATENT DOCUMENTS

WO    WO 98/22125    5/1999

OTHER PUBLICATIONS

Palayama, A. et al, "Synthesis of Substitued 6–Aminonaphthalene–1–Sulfamides", *The Lithuanian Academy of Sciences, Chemistry*, No. 3, (182), 1991, pp. 1–6, with translation.

Lawson et al., J. Biol. Chem. 267: pp. 4834–4843. 1992.

Buténas et al., Biochem. 31: pp. 5399–5411, 1992.

Buténas et al., Anal. Biochem. 225: pp. 231–241, 1995.

*Primary Examiner*—Christopher S. F. Low
*Assistant Examiner*—David Lukton
(74) *Attorney, Agent, or Firm*—McDonnell Boehnen Hulbert & Berghoff

(57) ABSTRACT

Compounds of the following formula are disclosed, wherein $R_1$ is a peptide and $R_2$ is an amino acid or peptide as disclosed herein:

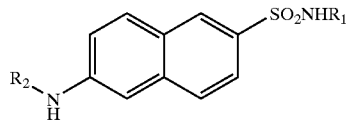

Figure 1:
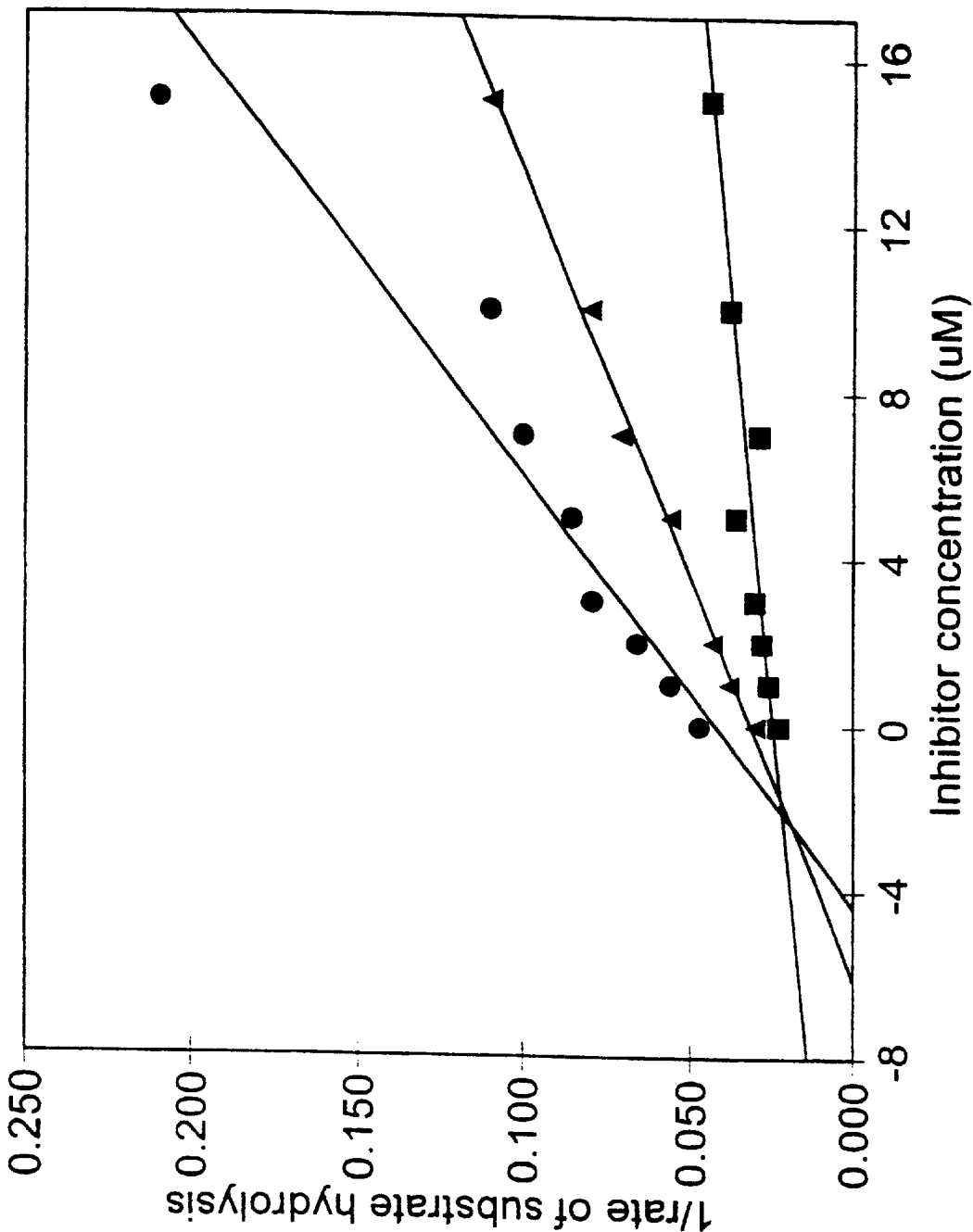

The compounds are inhibitors of activated protein C.

8 Claims, 8 Drawing Sheets

PEPTIDOMIMETICS CONTAINING 6-PEPTIDYLAMINO-1-NAPHTHALENESULFONAMIDE MOIETIES

This application claims the benefit of Provisional Application No. 60/031,359, filed Nov. 19, 1996.

BACKGROUND OF THE INVENTION

1. Field of the Invention

Broadly speaking, the present invention relates to novel compounds containing synthetic peptide moieties. More particularly, the invention relates to peptidomimetics of natural substrates for activated protein C (APC), which substrates are promoters of the blood coagulation process. The invention further relates to the use of such compounds in the inhibition of anticoagulation processes and the promotion of coagulation processes in blood.

2. Description of the Related Art

Activated protein C (APC) is a serine protease involved in blood coagulation and fibrinolysis. It can be described as trypsin-like in that it is protease which preferentially hydrolyzes peptide, ester, or amide bonds in which a basic amino acid provides the carbonyl group of the scissile bond. The in vivo specificity of this enzyme is a complex function of a variety of structural factors including binding domains in the protease for specific no acid side chains located on both the amino and carboxyl side of the targeted lysine or arginine residues in the substrate protein. The idea that short peptide substrates can be designed to incorporate enough information to discriminate among various proteases relies on the concept that each active site is comprised of a unique series of side chain binding pockets.

Lawson et al., (J. Biol. Chem. 267: 4834–4843, 1992), which is incorporated herein by reference, discusses the development of a fluorescent substrate [6-(Mes-D-Leu-Gly-Arg)amino-1-(dimethyl)naphthalenesulfonamide which can be used to directly measure the enzymatic activity of factor VIIa in the presence and absence of tissue factor and phospholipid.

Butenas et al., (Biochem. 31:5399–5411, 1992) which is incorporated herein by reference, describes 6-amino-1-naphthalenesulfonamides and 6-peptidylamimo-1-naphthalenesulfonamides useful in the detection of serine proteases involved in coagulation and fibrinolysis.

Butenas et al., (Chemistry, [Lithuanian Academy of Sciences] 182:144–153, 1992) which is incorporated herein by reference describes the synthesis of 6-amino-1-naphthalenesulfonamides and suggests that these compounds may be used as detecting groups in peptide substrates for proteases.

Butenas et al., (Anal. Biochem. 225:231–241, 1995) which is incorporated herein by reference describes various isomers of aminonaphthalenesulfonamides and peptidylaminonapthalenesulfonamides including 6-amino-2-naphthalenesulfonamide and 6-peptidyl-2-aminonaphthalenesulfonamide useful in the detection of APC.

U.S. Pat. No. 5,399,487 discloses compounds of the formula:

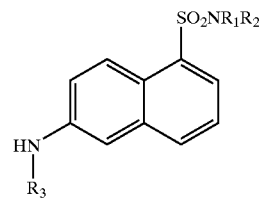

wherein
$R_1$ is hydrogen, lower alkyl, alkenyl, alkynyl, cycloalkyl, alkylcycloalkyl, cycloalkylalkyl, or phenylalkyl;
$R_2$ is hydrogen, alkyl, alkenyl, alkynyl, cycloalkyl, alkylcycloalkyl, cycloalkylalkyl, or phenylalkyl; or
$NR_1R_2$ forms a nitrogen heterocycle; and
$R_3$ is hydrogen, an amino acid or a peptide residue.
Those compounds are said to function as substrates in assays for determining proteolytic enzyme activity or as enzyme inhibitors.

SUMMARY OF THE INVENTION

The present invention provides compounds of formula I:

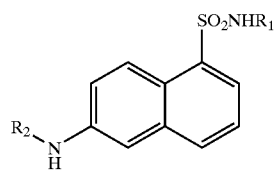

or the pharmaceutically acceptable salts thereof wherein:
$R_1$ is benzyl group or a peptide of the formula

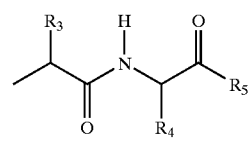

I wherein
$R_3$ and $R_4$ represents free or protected amino acid side chains, and $R_5$ hydroxy, alkoxy, benzoxy, and amino acid or peptide residue; and
$R_2$ is an amino acid or a peptide residue.
Compounds of formula I provide APC inhibitors having high specificity for this particular enzyme.
The present invention also provides compounds of formula II

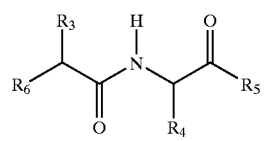

II or the pharmaceutically acceptable salts thereof wherein:
$R_3$, $R_4$ and $R_5$ are same as in formula I; and
$R_6$ is 6-aminonaphthalenesulfonamide attached to the peptide group via the sulfonamide nitrogen atom or either a free or protected amino group attached to the peptide group via a terminal nitrogen atom.

Compounds of formula I and II protect coagulation factors VIIa and Xa from the inhibition by tissue factor pathway inhibitor (TFPI). These compounds also enhance thrombin generation rate in a reconstituted in vitro model of blood coagulation.

The invention provides promoters of blood coagulation.

The compounds of formula I and II are highly selective inhibitors of the anticoagulation process in blood. The procoagulant activity is due, in part, to the inhibition of the anticoagulant pathways. Antithrombin III, APC and TFPI regulate blood coagulation in a negative fashion. Compounds of formula I that may be employed as inhibitors of the APC bind to this enzvme with high affinity but are hydrolyzed slowly or not at all. Consequently, the invention provides compounds useful in interfering or inhibiting the anticoagulation process in blood. Additionally. these compounds accelerate prothrombin activation in a reconstituted in vitro model of blood coagulation. As a summary of all three effects, compounds of formula I and II decrease clotting time of normal, factor VIII-deficient, and factor IX-deficient plasmas, as well as of whole blood.

BRIEF DESCRIPTION OF THE DRAWINGS

FIG. 1 is a graph of inhibitor concentration vs. rate of substrate hydrolysis showing the resulting inhibition constant ($K_i$) of Compound 1 for APC. Three different concentrations of chromogenic substrate Spectrozyme TH (100, 200, and 600 $\mu$M) were used in this assay.

FIG. 2 is a graph of time vs thrombin generation initiated by 0.5 pM factor VIIa/tissue factor. Open circles indicate all coagulation proteins present; filled circles indicate all coagulation proteins, protein C (PC), and thrombomodulin (Tm) present; open triangles indicate all coagulation proteins. PC, Tm, and compound #9 present; filled triangles indicate all coagulation proteins. PC, Tm, and compound #1 present.

FIG. 3 is a graph of time vs thrombin generation initiated by 1.25 pM factor VIIa/tissue factor. Filled squares indicate all coagulation proteins, PC, and Tm present; open squares indicate all coagulation proteins, PC, and Tm present, factor VIII absent; open diamonds indicate all coagulation proteins, PC, Tm, and compound #1 present, factor VIII absent; filled diamonds indicate all coagulation proteins, PC, Tm, and compound #9 present, factor VIII absent.

FIG. 4 is a graph of compounds #1 and #9 concentration vs factor VIIa/tissue factor activity. Open squares indicate factor VIIa/tissue factor and compound #9 present; filled squares indicated factor VIIa/tissue factor and compound #1 present; open circles indicate factor VIIa/tissue factor, compound #9, and tissue factor pathway inhibitor (TFPI) present; filled circles indicate factor VIIa/tissue factor, compound #1, and TFPI present.

FIG. 5 is a graph of compounds #1 and #9 concentration vs factor Xa activity. Open squares indicate factor Xa and compound #9 present; filled squares indicate factor Xa and compound #1 present; open circles indicte factor Xa, compound #9, and TFPI present; filled circles indicate factor Xa, compound #1, and TFPI present.

FIG. 6 is a graph of time vs thrombin generation initiated by 1.25 pM factor VIIa/tissue factor. Open circles indicate all coagulation proteins and TFPI present; filled circles indicate all coagulation proteins and TFPI present, factor VIII absent; open triangles indicate all coagulation proteins, TFPI, and compound #9 present, factor VIII absent; filled triangles indicate all coagulation proteins, TFPI, and compound #1 present, factor VIII absent.

FIG. 7 is a graph of time is thrombin generation initiated by 1.25 pM factor VIIa/tissue factor. Open circles indicate all coagulation proteins, PC, Tm, and TFPI present; filled circles indicate all coagulation proteins, PC, Tm, and TFPI present, factor VIII absent; open triangles indicate all coagulation proteins, PC, Tm, TFPI, and compound #9 present, factor VIII absent; filled triangles indicate all coagulation proteins, PC, Tm, TFPI, and compound #1 present, factor VIII absent; squares indicate all coagulation proteins, PC, Tm, TFPI, and compounds #1 and #9 present, factor VIII absent.

FIG. 8 is a graph of time vs thrombin generation initiated by 1.25 pM factor VIIa/tissue factor. Open circles indicate all coagulation proteins present; filled circles indicte all coagulation proteins and compound #1 present; triangles indicate all coagulation proteins and compound #9 present; squares indicate all coagulation proteins and compound #26 present.

DETAILED DESCRIPTION OF THE INVENTION

The present invention provides compounds of formula I:

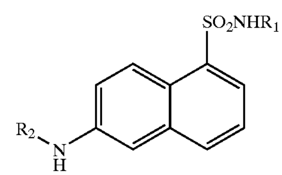

or the pharmaceutically acceptable non-toxic salts thereof; wherein $R_1$ is benzyl group or a peptide of the formula 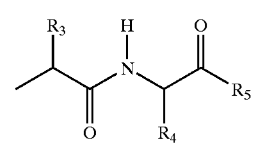 wherein $R_3$ and $R_4$ represents free or protected amino acid side chains, and $R_5$ hydroxy, alkoxy, benzoxy, and amino acid or peptide residue; and $R_2$ is an amino acid or a peptide residue.

Compounds of formula I provide APC inhibitors having high specificity for this particular enzyme.

The present invention also provides compounds of formula II 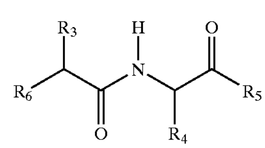 or the pharmaceutically acceptable salts thereof wherein:

$R_3$, $R_4$ and $R_5$ are same as in formula I; and $R_6$ is 6-aminonaphthalenesulfonamide attached to the peptide group via the sulfonamide nitrogen atom or either a free or protected amino group attached to the peptide group via a terminal nitrogen atom.

The invention also provides compounds of formuia III

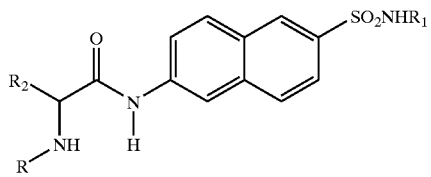

wherein
$R_1$ is as defined above for formula I;
R represents an amino acid or a peptide residue; and
$R_2$ represents the side chain of L-arginine, D-arginine, homoarginine or β-homoarginine.

Representative compounds of the present invention, which are encompassed by formula I, include their non-toxic pharmaceutically acceptable salts.

Non-toxic pharmaceutically acceptable salts include salts of acids such as, for example, hydrochloric, phosphoric, hydrobromic, sulfuric, sulfinic, formic, toluene sulfonic, hydroiodic, acetic, trifluoroacetic and the like. Those skilled in the art will recognize a wide variety of non-toxic pharmaceutically acceptable additional salts.

The compounds of the invention are conveniently synthesized in relatively high yields using the methods described in U.S. Pat. No. 5,399,487, which is herein incorporated by reference in its entirety, in addition to any of a variety of synthetic methodologies known in the art. An exemplary synthetic scheme is set forth below in Schemes I–II.

By peptide residue is meant a group comprising at least two amino acids coupled, for example, by an α peptide bond. The peptide residues of the invention may be obtained by proteolytic processing of an existing natural product, chemical synthesis from blocked amino acids or by molecular biological approaches using cells in vitro. An amino acid, or the amino acids used in the preparation of the peptide residues, may be either naturally or non-naturally occurring amino acids. The peptide residues may optionally contain various amino or carboxy protecting groups. Representative protecting groups are the "BOC" group, i.e., t-butoxycarbonyl, the "Z" group, i.e., benzyloxycarbonyl, the "FMOC" group i.e., fluorenylmethoxycarbonyl, the "Bz" group, i.e., benzyl, the "Et" group, i.e., ethyl, the "Me" group, i.e., methyl, and the "Bzl" group, i.e., benzoyl.

By inhibitor for a proteolytic enzyme is meant a compound of formula I that interacts with high affinity toward a serine protease and block active site of enzyme.

By amino acid side chain is meant a substituent on the carbon alpha to the amino acid carboxy group.

The blood coagulation cascade is triggered when subendothelial derived tissue factor is exposed as a consequence of vascular damage and forms an enzymatic complex with the plasma serine protease, factor VIIa. The factor VIIa/tissue factor complex activates factor X and factor IX to the enzymes factor Xa and factor IXa. Factor IXa in complex with its cofactor, factor VIIIa, activates factor X at an approximately 50-fold higher rate than the factor VIIa/tissue factor complex. In turn, factor Xa may activate factor VII and further enhance factor IX and factor X activation. The major function of factor Xa is to form the prothrombinase complex with factor Va and a phospholipid membrane surface leading to the activation of prothrombin to thrombin. Thrombin cleaves soluble fibrinogen, forming fibrin which polymerizes to form an insoluble clot. The blood coagulation cascade is downregulated by natural inhibitors of blood coagulation: tissue factor pathway inhibitor (TFPI), activated protein C (APC) and antithrombin III (AT-III).

Essential cofactors of blood coagulation cascade, factors V(a) and VIII(a), are cleaved at the sites presented in Table 1. As the result of these cleavages, the cofactor function is lost. TFPI inhibits coagulation enzymes factors VIIa and Xa.

TABLE 1

The sequence of APC natural substrate cleavage sites.

| Sequence | Substrate | Cleavage Site |
|---|---|---|
| $P_4$—$P_3$—$P_2$—$P_1$—$P_1'$—$P_2'$—$P_3'$—$P_4'$ | | |
| 1. -Lys-Lys-Thr-Arg-Asn-Pro-Lys-Lys [SEQ ID NO.1] | factor V/Va | $Arg^{306}$ |
| 2. -Leu-Asp-Arg-Arg-Gly-Ile-Gln-Arg- [SEQ ID NO.2] | factor V/Va | $Arg^{506}$ |
| 3. -Met-Ala-Thr-Arg-Lys-Met-His-Asp- [SEQ ID NO.3] | factor V/Va | $Arg^{678}$ |
| 4. -Arg-Leu-Lys-Lys-Ser-Gln-Phe-Leu- [SEQ ID NO.4] | factor V | $Arg^{994}$ |
| 5. -Pro-Gln-Leu-Arg-Met-Lys-Asn-Asn- [SEQ ID NO.5] | factor VIII/VIIIa | $Arg^{336}$ |
| 6. -Val-Asp-Gln-Arg-Gly-Asn-Gln-Ile- [SEQ ID NO.6] | factor VIII/VIIIa | $Arg^{562}$ |
| 7. -Ile-Glu-Pro-Arg-Ser-Phe-Ser-Gln- [SEQ ID NO.7] | factor VIII | $Arg^{740}$ |

Any compound which will be able to specifically inhibit APC and to suppress the action of TFPI, would be beneficial to treatment of hemophilia A and hemophilia B.

The compounds of formula I and II are highly selective inhibitors for APC (see examples 2 and 3). The compounds of formula I, II and III may protect coagulation enzymes from the inactivation by TFPI (see example 3), and are able to promote thrombin generation in a reconstituted in vitro model of blood coagulation (see example 4). The compounds of the invention can be used to inhibit APC, to inactivate TFPI, and to promote the blood coagulation cascade. Such compounds will act as competitive, specific inhibitors of APC to reduce the rate of reaction of this protease with it natural substrates factors V(a) and VIII(a), and, thus, will reduce natural proteolytic activity of this enzyme either in vivo or in vitro. Such compounds will also protect factors VIIa and Xa from inhibition by TFPI. They will promote the blood coagulation process due to the acceleration of thrombin generation.

Compounds in which hydrolysis of the 6-aminoacyl bond is slow (relative to that of other compounds in the series) are particularly useful as inhibitors. Whether a given compound of the invention will be efficient and specific inhibitor of the enzyme can readily be determined by measurement of inhibition constants. See, for example, Alan Fersht, *Enzyme Structure and Mechanism*, W. H. Freeman and Company, New York, 1985, which is herein incorporated by reference, for a discussion of techniques by which these binding parameters cain be measured.

The overall efficacy of compounds of formula I–III can be determined in a reconstituted model of blood coagulation [J. H. Lawson et al., J. Biol. Chem. 269, 23357–23366 (1994)] in a clotting assay or in a whole blood coagulation analysis—Rand et al., Blood 88, 3432–3445 (1996).

All of these aspects of the invention can be practiced by administration of the compound to any patient who would benefit by an increase in clotting rates because of the interactions described above. The compounds are particularly useful in treatment of any disease or disorder that would be ameliorated by enhancing of the action of thrombin with existing medications, including both platelet driven (arterial) and thrombin driven (veneous) clotting processes, such as the treatment of bleeding associated with congenital and acquired hemophilia and mechanical trauma.

When used in vitro, the compositions are used in the same manner and in place of other currently available procoagulants.

The compounds of formula I, II and III may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmacetical formulation comprising a compound of formula I, II and III and a pharmaceutically acceptable carrier. One or more compounds of formula I and II may be present in association with one or more non-toxic pharmaceutically acceptable carriers and/or diluent and/or adjuvants and if desired other active ingredients. The pharmaceutical compositions containing compounds of formula I, II and III may be in form suitable for oral use, for example, as tablets, troches, lozenges, aqueous or oily suspensions, dispersible powers or granules, emulsion, hard or son capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of formula I, II and III may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of formula I and II may be administered parenterally in a sterile medium. The drug, depending on the vehicle and concentration used, can either be suspended or dissolved in the vehicle. Advantageously, adjuvants such as a local anaesthetic, preservative and buffering agents can be dissolved in the vehicle.

Dosage levels of the order of from about 0.1 mg to about 140 mg per kilogram of body weight per day are useful in the treatment of the above-indicated conditions (about 0.5 mg or about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration and rate of excretion.

An illustration of the synthesis of the compounds of the present invention is shown on the basis of compound 24 (Example 1) in schemes I and II. Those having skill in the art will recognize that the starting materials may be varied and additional steps employed to produce compounds encompassed by the present invention, as demonstrated by the following examples.

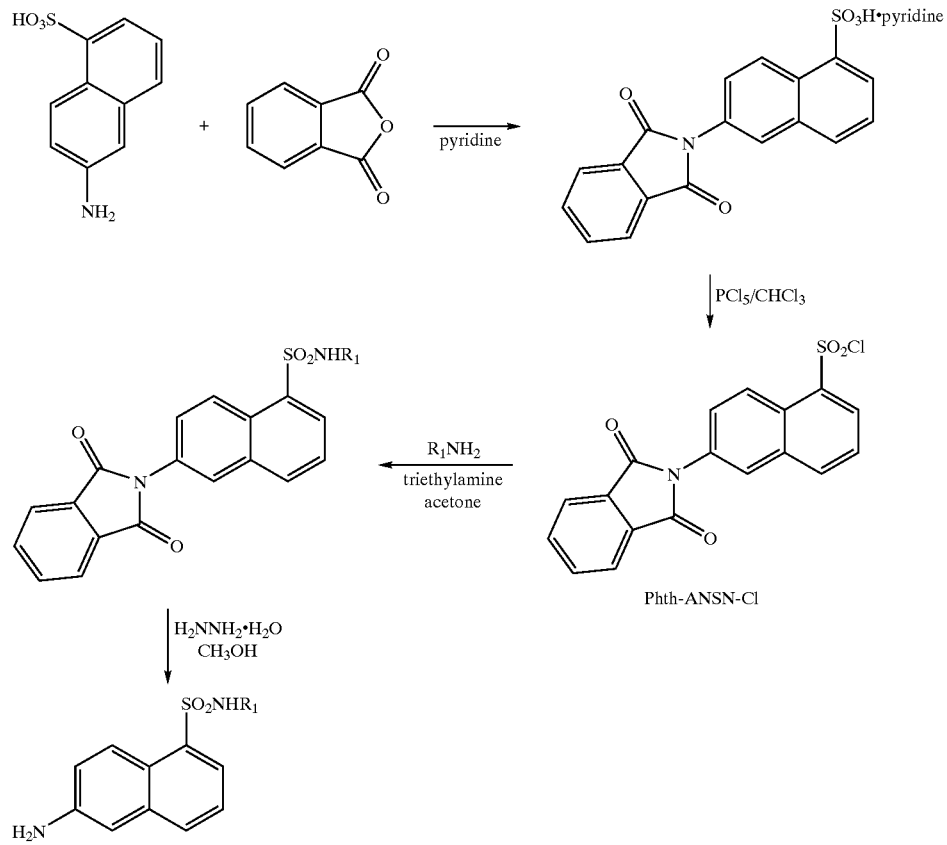

Scheme I

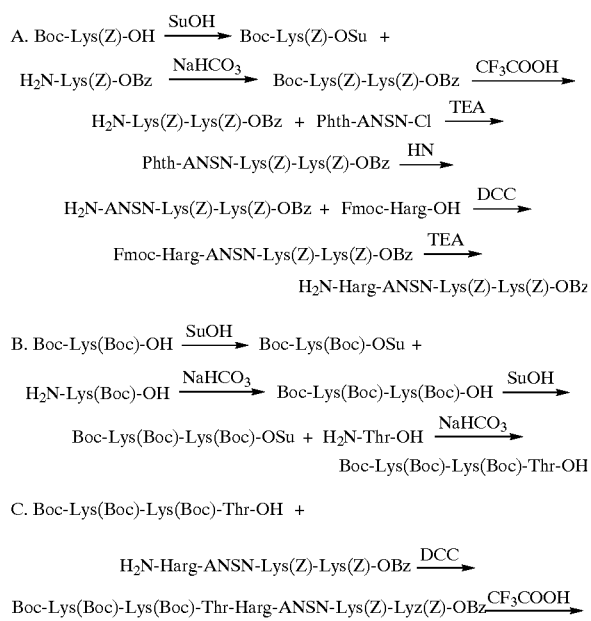

Scheme II

-continued

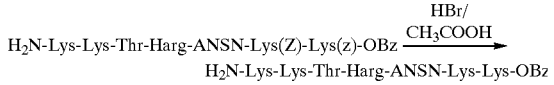

where

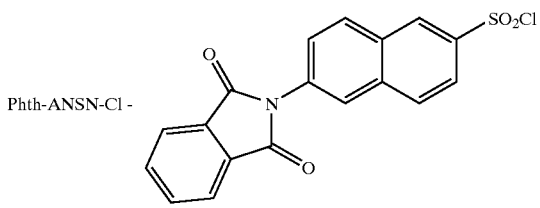

SuOH—N-Hydroxysuccinimide
DCC—1,3-Dicyclohexylcarbodiimide
TEA—Triethylamine
HH—Hydrazine monohydrate The disclosures in this application of all articles and references, including patents, are incorporated herein by reference.

The invention is illustrated further by the following examples which are not be construed as limiting the invention in scope or spirit to the specific compounds or procedures described in them.

EXAMPLE 1

Peptides are prepared according to Anderson, G. W., Zimmerman, J. E. & Callahan, F. H. (1964) *J. Am. Chem. Soc.* 86:1839–1842, 6-Peptidylamino-2-naphthalenesulfonamides are prepared essentially according to the methods described in U.S. Pat. No. 5,399,487 together with methods known in the art. Reactive groups, e.g., free nitrogens, are protected as necessary.

Synthesis of H-Lys-Lys-Thr-Harg-ANSN-Lys-Lys-OH [SEQ ID NO.8] (a typical procedure for all compounds present in this invention) (Schemes I and II).

A. Synthesis of Boc-Lys(Boc)-Lys(Boc)-Thr-OH. Equimolecular amounts of Boc-Lys(Boc)-OH and N-hydroxysuccinimide were dissolved in dry 1,4-dioxane, the solution was cooled to 4° C., and an equimolecular amount of 1,3-dicyclohexylcarbodiimide (DCC) was added. The reaction mixture was kept overnight at 4° C., precipitated 1,3-dicyclohexylurera (DCU) was filtered, and the filtrate was evaporated to dryness. The succinimide ester of di-Boc-lysine was crystallized from iso-propanolyhexane. This ester was dissolved in dry 1,4-dioxane and added to a water solution of equimolecular amount of $H_2N$-Lys(Boc)-ONa and $NaHCO_3$. The reaction mixture was kept overnight at room temperature, 1,4-dioxane was evaporated, and the residual solution was acidified with conc. HCl to pH 2. Precipitated Boc-Lys(Boc)-Lys(Boc)-OH was filtered, washed with water and dried. This dipeptide was dissolved in dry 1,4-dioxane, an equimolecular amount of N-hydroxysuccinimide was added, the solution was cooled to 4° C., and an equimoiecular amount of DCC was added. The reaction mixture was kept overnight at 4° C., precipitated DCU was filtered, and the filtrate was evaporated to dryness. Succinimide ester Boc-Lys(Boc)-Lys(Boc)-OSu was crystallized from iso-propanol/hexane. This ester was dissolved in dry 1,4-dioxane and added to a water solution of equimolecular amount of $H_2N$-Thr-ONa and $NaHCO_3$. The reaction mixture was kept overnight at room temperature, 1,4-dioxane was evaporated, and the residual solution was acidified with conc. HCl to pH 2. Precipitated Boc-Lys(Boc)-Lys(Boc)-Thr-OH was filtered, washed with water and dried.

B. Synthesis of Harg-ANSN-Lys(Z)-Lys(Z)-OBz hydrochloride. The succinimide ester of Boc-Lys(Z)-OH and dipeptide Boc-Lys(Z)-Lys(Z)-OBz were prepared as described in part A. The dipeptide was dissolved in trifluoroacetic acid, the solution was kept for one hour at room temperature, and poured into dry diethyl ether. Precipitated $H_2N$-Lys(Z)-Lys(Z)-OBz trifluoroacetate was filtered, washed with diethyl ether and dried. This dipeptide was dissolved in acetone, two equivalents of triethylamine and one equivalent of 6-phthalimido-2-naphthalenesulfonyl chloride were added. The reaction mixture was kept for 8 hr at room temperature, acetone was evaporated, and the residual was treated with water. Precipitated phthalimido-ANSN-Lys(Z)-Lys(Z)-OBz was filtered, washed with water, and dried. This compound was dissolved in methanol, the solution was heated to boiling, and two equivalents of hydrazine hydrate were added. The reaction mixture was kept at room temperature for 16 hr, precipitated phthalhydrazide was filtered, and filtrate was evaporated to dryness. The ANSN-Lys(Z)-Lys(Z)-OBz was crystallized from methanol, filtered, dried and used in the next step. This compound and an equimolecular amount of Fmoc-Harg-OH hydrochloride were dissolved in dry pyridine, cooled to −20° C., and an equimolecular amount of DCC was added. The reaction mixture was kept for 0.5 hr at −20° C., for 2 hr at 4° C. and for 16 hr at room temperature. The precipitated DCU was filtered, pyridine was evaporated, and the residual oil was dissolved in $CHCl_3$—PrOH (3:1). This solution was washed with water, 2N HCl, 2% $N_4H$ OH and with water again, dried over anhydrous $Na_2SO_4$, and evaporated to dryness. The Fmoc-Harg-ANSN-Lys(Z)Lys(Z)-OBz hydrochloride was crystallized from iso-propanol. This compound was dissolved in dimethylformamide (DMFA), the excess of triethylamine was added, and the reaction mixture was kept at room temperature overnight. DMFA was evaporated and Harg-ANSN-Lys(Z)-Lys(Z)-OBz hydrochloride was precipitated with dry diethyl ether.

C. Synthesis of H-Lys-Lys-Thr-Harg-ANSN-Lys-Lys-OH [SEQ ID NO.8]. Equimolecular amounts of Boc-Lys(Boc)-Lys(Boc)-Thr-OH and 1-hydroxybenzotriazole were dissolved in DMFA, the solution was cooled to −20° C., and an equimolecular amount of DCC was added. The reaction mixture was kept for 1 hr at 4° C. An equimolecular solution of Harg-ANSN-Lys(Z)-Lys(Z)-OBz hydrochloride in DMFA was added, and the reaction mixture was kept at 4° C. for 1.5 hr and at room temperature for 17 hr. Precipitated DCU was filtered, solvent evaporated, and the residual oil was dissolved in n-butanol-ethyl acetate (1:1). This solution was washed with 5% $NaHCO_3$, 10% $KHSO_4$, and water. The organic solution was concentrated, and Boc-Lys(Boc)-Lys(Boc)-Thr-Harg-ANSN-Lys(Z)-Lys(Z)-OBz [SEQ ID NO.9] was precipitated with dry diethyl ether. The dried product was dissolved in pyridinium polyhydrogen fluoride, anisole was added, and the solution was kept at room temperature for 1 hr. HF and pyridine were evaporated, and the residual was treated with 0.2N acetic acid. Precipitated crude H-Lys-Lys-Thr-Harg-ANSN-Lys-Lys-OH [SEQ ID NO.8] hexaacetate was filtered, washed with water and dried.

Purification of synthesized compounds was accomplished by chromatography over a Sephadex LH-20 column (1×100 cm) using methanol as an eluant.

The following compounds were synthesized essentially according to the procedures described above.

| | |
|---|---|
| Compound 1 | Lys-Lys-Thr-Harg-ANSN-Lys(Z)-Lys(Z)-OBz [SEQ ID NO.8] |
| Compound 2 | Val-Leu-Harg-ANSN-Bz |
| Compound 3 | Boc-Ser-Trp-Arg-Harg-ANSN-Ser-Glu(OBz)$_2$ [SEQ ID NO.10] |
| Compound 4 | Boc-Val-Asp(Me)-Gln-Harg-ANSN-Glu-Ile-OBz [SEQ ID NO. 11] |
| Compound 5 | Boc-Leu-Asp(Me)-Arg-Harg-ANSN-Gln-Arg-OEt [SEQ ID NO.12] |
| Compound 6 | Leu-Asp(Me)-Arg-Harg-ANSN-Gln-Arg-OEt [SEQ ID NO.12] |
| Compound 7 | Pro-Glu-Leu-Harg-ANSN-Asn-Asn-OBz [SEQ ID NO.13] |
| Compound 8 | Ile-Glu(OBz)-Pro-Harg-Asn-Ser-Glu-OBz [SEQ ID NO.14] |
| Compound 9 | Harg-ANSN-Lys(Z)-Lys(Z)-OBz |
| Compound 10 | Boc-Lys(Boc)-Lys(Boc)-Thr-Harg-ANSN-Lys(Z)-Lys(Z)-OBz [SEQ ID NO.9] |
| Compound 11 | oc-Lys(Boc)-Lys(Boc)-Thr-Harg-ANSN-Lys(Boc)-Lys(Z)-OBz [SEQ ID NO.9] |
| Compound 12 | Boc-Lys(Boc)-Lys(Boc)-Thr-Harg-ANSN-Lys(Boc)-Lys(Boc)-OMe [SEQ ID NO.9] |
| Compound 13 | Lys-Lys-Thr-Harg-ANSN-Bz [SEQ ID NO.8] |
| Compound 14 | Lys-Lys(Z)-Thr-Harg-ANSN-Lys(Z)-OBz [SEQ ID NO.15] |
| Compound 15 | Lys(Z)-Lys(Z)-Thr-Harg-ANSN-Lys(Z)-OBz [SEQ ID NO.16] |
| Compound 16 | Z-Lys-Lys-Thr-Harg-ANSN-Lys(Z)-Lys(Z)-OBz [SEQ ID NO.8] |
| Compound 17 | Z-Lys-Lys-Thr-(β-Harg)-ANSN-Lys(Z)-Lys(Z)-OBz [SEQ ID NO.17] |
| Compound 18 | Z-Lys-Lys-Thr-(D-Arg)-ANSN-Lys(Z)-Lys(Z)-OBz [SEQ ID NO.18] |
| Compound 19 | Z-Lys-Lys(Z)-Thr-Harg-ANSN-Lys(Z)-Lys(Z)-OBz [SEQ ID NO.15] |
| Compound 20 | Lys(Z)-Lys(Z)-Thr-Harg-ANSN-Lys(Z)-Lys(Z)-OBz [SEQ ID NO.16] |
| Compound 21 | Z-Lys-Lys-Thr(OBz)-Harg-ANSN-Lys(Z)-Lys(Z)-OBz [SEQ ID NO.19] |
| Compound 22 | Lys-Lys-Thr-Harg-ANSN-Lys-Lys(Z)-OBz [SEQ ID NO.8] |
| Compound 23 | Lys-Lys-Thr-Harg-ANSN-Lys-Lys-OMe [SEQ ID NO.8] |
| Compound 24 | Lys-Lys-Thr-Harg-ANSN-Lys-Lys-OBz [SEQ ID NO.8] |
| Compound 25 | ANSN-Lys(Z)-Lys(Z)-OBz |
| Compound 26 | H$_2$N-Lys(Z)-Lys(Z)-OBz |
| Compound 27 | Boc-Lys(Z)-Lys(Z)-Thr-OH |
| Compound 28 | Phth-ANSN-Lys(Z)-Lys(Z)-OBz |
| Compound 29 | Boc-Lys(Z)-Lys(Z)-OBz |
| Compound 30 | Boc-Lys(Z)-Lys(Z)-OH |
| Compound 31 | H$_2$N-Lys(Z)-Lys(Z)-Thr-OH |
| Compound 32 | Z-Lys(Boc)-Lys(Z)-Thr(Bz)-OH |
| Compound 33 | ANSN-CH$_2$C$_6$H$_5$ |
| Compound 34 | ANSN-Ser-Ser-OBz |
| Compound 35 | H$_2$N-Ser-Ser-OBZ |
| Compound 36 | ANSN-Gln-Ile-OBz |
| Compound 37 | ANSN-Asn-Asn-OBZ |
| Compound 38 | ANSN-Ser-Glu-OBz |
| Compound 39 | Boc-Lys(Z)-Lys(Z)-Thr-Harg-ANSN-Lys(Z)-Lys(Z)-OBz [SEQ ID NO.16] |

Preferred compounds of the invention are Compounds Nos. 27, 28, 38, 18, 17, and 37 (listed in decreasing order of preference). Particularly preferred compounds of the invention are Compounds Nos. 1, 25, 29, 36, 33, and 9 (listed in decreasing order of preference).

EXAMPLE 2
Inhibition Constant Assay

A 10 mM solution of inhibitor in methyl sulfoxide was prepared and then was diluted to 100 μM with HBS. Various amounts of the resulting 100 μM solution were added to HBS containing 100 μM Spectrozyme TH. The final concentrations of inhibiter were 0, 1, 2, 3, 5, 7, 10, and 15 μM. APC was added to a final concentration of 5 nM, and the rate of substrate hydrolysis was monitored. The inverse raw of substrate hydrolysis was calculated and plotted vs inhibitor concentration as shown in FIG. 1.

The experiment was repeated using 200 μM and 600 μM Spectrozyme TH. The concentrations of inhibitor and APC were as in the first experiment. The inverse rates of substrate hydrolysis were again plotted vs inhibitor concentrations. The intersection of these three plots gives the inhibition constant value (2.1 μM).

$K_i$'s for compounds of the invention are shown below in Table 2.

TABLE 2

| Compound | $K_i$:APC | $K_i$:IIa | $K_i$:Xa |
|---|---|---|---|
| Compound 1 | 2.1 μM | >5 mM | 400 μM |
| Compound 3 | 35 μM | | |
| Compound 4 | 118 μM | | |
| Compound 5 | 160 μM | | |
| Compound 6 | 650 μM | | |
| Compound 7 | 550 μM | | |
| Compound 8 | 115 μM | | |
| Compound 9 | 90 μM | 1.5 mM | 150 μM |
| Compound 10 | 39 μM | | |
| Compound 11 | 28 μM | | |
| Compound 12 | 29 μM | | |
| Compound 13 | 280 μM | | |
| Compound 14 | 1.6 μM | >5 mM | 440 μM |
| Compound 15 | 1.8 μM | >5 mM | 440 μM |
| Compound 16 | 1.3 μM | NI | 740 μM |
| Compound 17 | 2.3 μM | | |
| Compound 18 | 1.1 μM | >5 mM | 280 μM |
| Compound 19 | 1.5 μM | NI | 230 μM |
| Compound 20 | 4.5 μM | NI | 330 μM |
| Compound 21 | 1.2 μM | >5 mM | 660 μM |
| Compound 22 | 8.8 μM | >5 mM | 2.2 μM |
| Compound 23 | 15 μM | NI | 170 μM |
| Compound 24 | 7.9 μM | 3.1 mM | 280 μM |

Analysis of the inhibition constants of 17 compounds (compounds 1 and 9–24) which contain a similar backbone structure and varying protecting groups (Table 2) demonstrates that all these compounds inhibit APC and factor Xa competitively. Inhibition constants for APC vary in a wide range for 1.1 μM for compound 18 to 280 μM for compound 13. These constants show a strong dependence on the inhibitor's P and P' structure and on the location of blocking groups in these structures. Compound 9, which contains only Harg in the P structure, is a relatively poor inhibitor of APC and has relatively high $K_i$ (90 μM). On the other hand, compound 13 which contains the $P_1$–$P_4$ structure of factor V/Va Arg$^{306}$ cleavage site and aminonaphthalenebenzylsulfonamide in the P' structure, displays significantly lower affinity to APC with 280 μM $K_i$. Compounds 10–12 which contain $P_1$–$P_4$, $P_3'$ and $P_4'$ structure of the Arg$^{306}$ cleavage site, have a $K_i$ in the range from 28 μM to 39 μM. It is necessary to emphasize that all functional groups of these three inhibitors are completely blocked by various protecting groups. Selective elimination of blocking groups leads to increased efficiency of synthesized inhibitors. Thus, compounds 23 and 24, with only their C-terminal carboxyl function blocked, have lower $K_i$. (15 μM and 7.9 μM respectively) than their completely blocked analogs mentioned above. Additionally, comparison of these two compounds (23 and 24) $K_i$'s demonstrates that an aromatic benzyl group is preferable to an aliphatic methyl group. Further analysis of the blocking groups' influence on inhibitor affinity to APC leads to the conclusion that compounds which contain at least one unblocked side-chain of Lys in the P structure and completely blocked functional groups in the P' structure have the highest affinity to APC (compounds 1, 14–19). The $K_i$ of these inhibitors for APC vary from 1.1 μM to 2.3 μM and is not influenced by the location ($P_3$ or $P_4$) of Lys with an unblocked side-chain (compare compounds 15 and 19). Moreover, simultaneous elimination of the blocking groups from the side-chains of both Lys (compounds 16–18) or, in addition, from N-terminal amino group (compound 1) does not cause any significant changes in the inhibitor's affinity to APC. However, when side-chains of both Lys are blocked and only the N-terminal amino group of $P_4$ Lys is unblocked, the inhibitor has a slightly elevated $K_i$ (compound 20; $K_i$ 4.5 μM). Blocking of $P_2$ Thr side-chain with a benzyl protecting group has no influence on the inhibitor's affinity to APC (compare compounds 16 and 21). Inhibitors created by substitution of Harg in the $P_1$ position with β-Harg (compound 17) or D-Arg (compound 18) possess a $K_i$ similar to that of initial compound 16 (2.3 μM, 1.1 μM, and 1.3 μM respectively). All inhibitors presented in Table 2 are poor inhibitors of factor Xa ($K_i$ ratio for factor Xa/APC reaches as much as 570 for compound 16) and (almost) do not inhibit thrombin.

EXAMPLE 3

Figure 2:
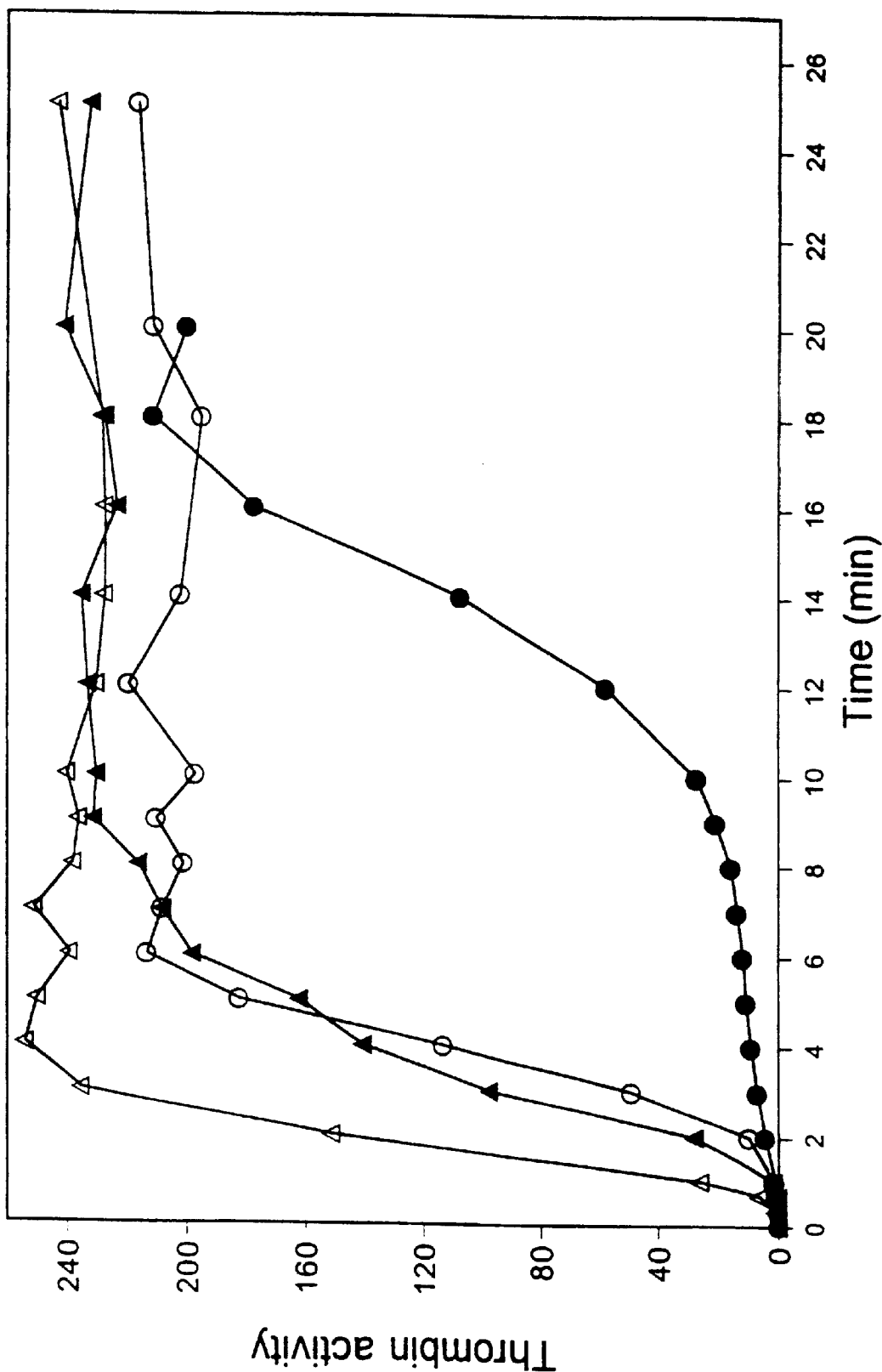

This tissue factor pathway to thrombin experiment was conducted to establish the influence of compounds 1 and 9 on thrombin generation in a reconstituted model of blood coagulation in the presence of protein C (PC) pathway (FIG. 2).

Tissue factor (0.5 nM) was relipidated into 400 μM of PCPS vesicles composed of 75% phosphatidylcholine (PC) and 25% phosphatidylserine (PS). The relipidated tissue factor was incubated with 1.0 pM factor VIIa in HBS (20 mM HEPES, 0.15M NaCl, 2 mM CaCl, pH 7.4) for 20 min at 37° C. to form factor VIIa/tissue factor complex. Other proteins were used at plasma concentrations. 20 nM factor V, 0.7 nM factor VIII, and 10 nM thrombomodulin were added to the factor VIIa/tissue factor complex. The initiation of the reaction was started by the addition of a zymogen and inhibitor mixture: 1.4 μM prothrombin, 170 nM factor X, 90 nM factor IX, 70 nM PC, and 40 μM compound 1 or 9 (all concentrations final). In the control experiments inhibitors were absent. Final concentration of factor VIIa was 0.5 pM, final concentration of tissue factor was 0.25 nM. At selected time points, 5 μl aliquots were removed and quenched into 40 mM EDTA in TBS (20 mM Tris, 0.15M NaCl, pH 7.4) for thrombin amidolytic activity assays employing 200 μM chromogenic substrate Spectrozyme TH.

EXAMPLE 4

Figure 3:
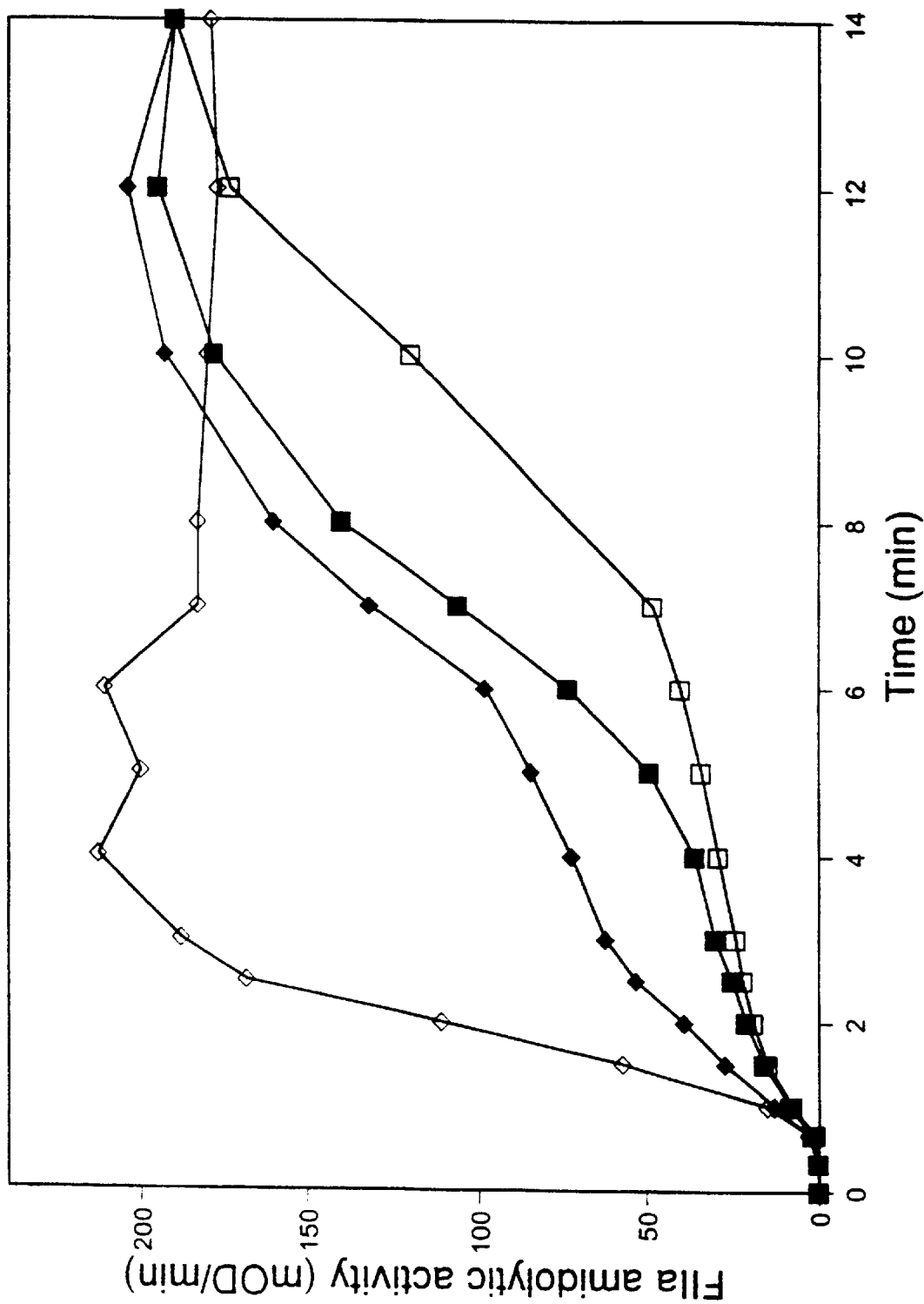

This tissue factor pathway to thrombin experiment was conducted to establish the influence of compounds 1 and 9 on thrombin generation in a reconstituted model of blood coagulation in the presence of APC pathway and in the absence of factor VIII (FIG. 3).

Tissue factor (0.5 nM) was relipidated into 400 μM PCPS vesicles composed of 75% phosphatidylcholine (PC) and 25% phosphatidylserine (PS). The relipidated tissue factor was incubated with 2.5 pM factor VIIa in HBS (20 mM HEPES, 0.15M NaCl, 2 mM CaCl, pH 7.4) for 20 min at 37° C. to form factor VIIa/tissue factor complex. Other proteins were used at plasma concentrations. 20 nM factor V and 10 nM thrombomodulin were added to the factor VIIa/tissue factor complex. The initiation of the reactions was started by the addition of a zymogen and inhibitor mixture: 1.4 μM prothrombin, 170 nM factor X, 90 nM factor IX, 70 nM protein C, and 40 μM compounds 1 or 9 (all concentrations final). In the control experiments factor VIII was present and inhibitors were absent. Final concentration of factor VIIa was 1.25 pM, final concentration of tissue factor was 0.25 nM. At selected time points, 5 μl aliquots were removed and quenched into 40 mM EDTA in TBS (20 mM Tris 0.15M NaCl, pH 7.4) for thrombin amidolytic activity assays employing 200 μM chromogenic substrate Spectrozyme TH.

EXAMPLE 5

Figure 4:
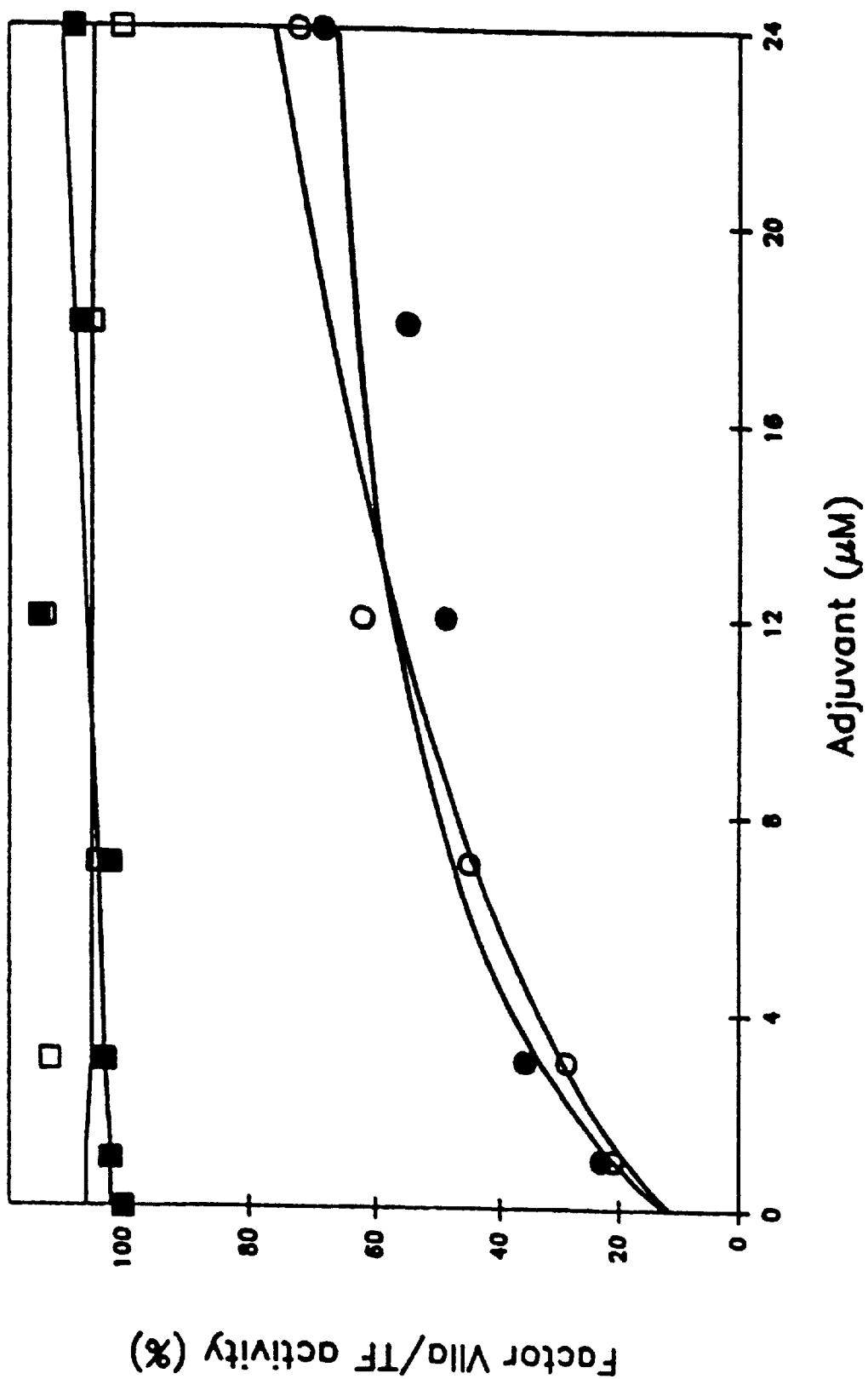

This tissue factor pathway inhibitor (TFPI) experiment was conducted to establish the influence of compounds 1 and 9 on the factor VIIa/tissue factor inhibition by TFPI (FIG. 4).

Tissue factor (10 nM) was relipidated into 200 μM of PCPS vesicles composed of 75% phosphatidylcholine (PC) and 25% phosphatidylserine (PS). The relipidated tissue factor was incubated with 4 nM factor VIIa in HBS (20 mM HEPES, 0.15M NaCl, 2mM CaCl, pH 7.4) for 20 min at 37° C. to form factor VIIa/tissue factor complex. 8 nM TFPI and inhibitor at selected concentrations (0–24 μM) were added to the factor VIIa/tissue factor complex, the mixture was incubated for 2 min, and amidolytic activity of enzymatic complex was evaluated by the rate of hydrolysis of 200 μM chromogenic substrate Spectrozyme Xa.

EXAMPLE 6

Figure 5:
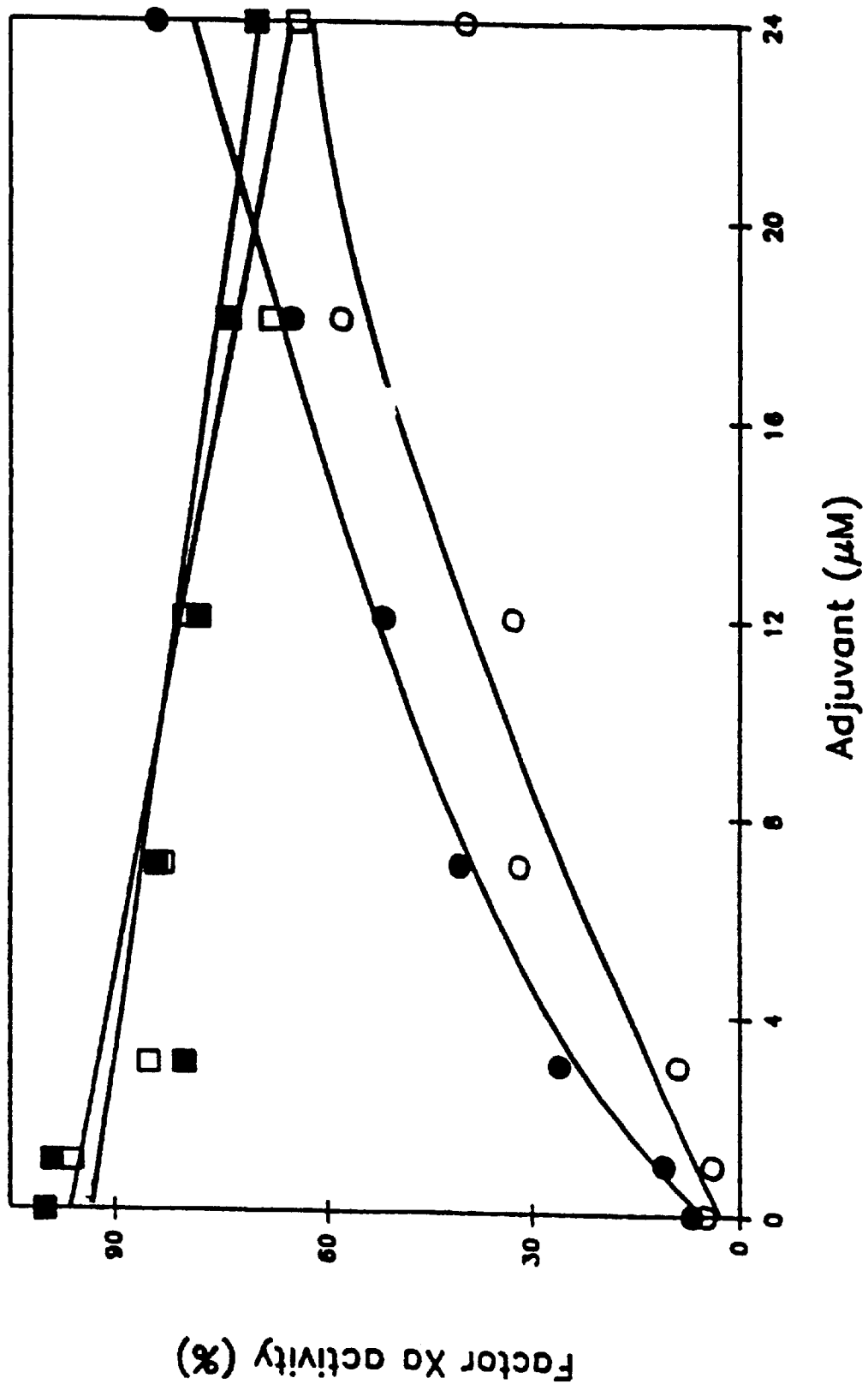

This tissue factor pathway inhibitor (TFPI) experiment was conducted to establish the influence of compounds 1 and 9 on the factor Xa inhibition by TPPI (FIG. 5).

8 nM TFPI and inhibitor at selected concentrations (0–24 μM) were added to 4 nM factor Xa in HBS, the mixture was incubated for 2 min, and amidolytic activity of factor Xa was evaluated by the rate of hydrolysis of 200 μM chromogenic substrate Spectrozyme Xa.

EXAMPLE 7

Figure 6:
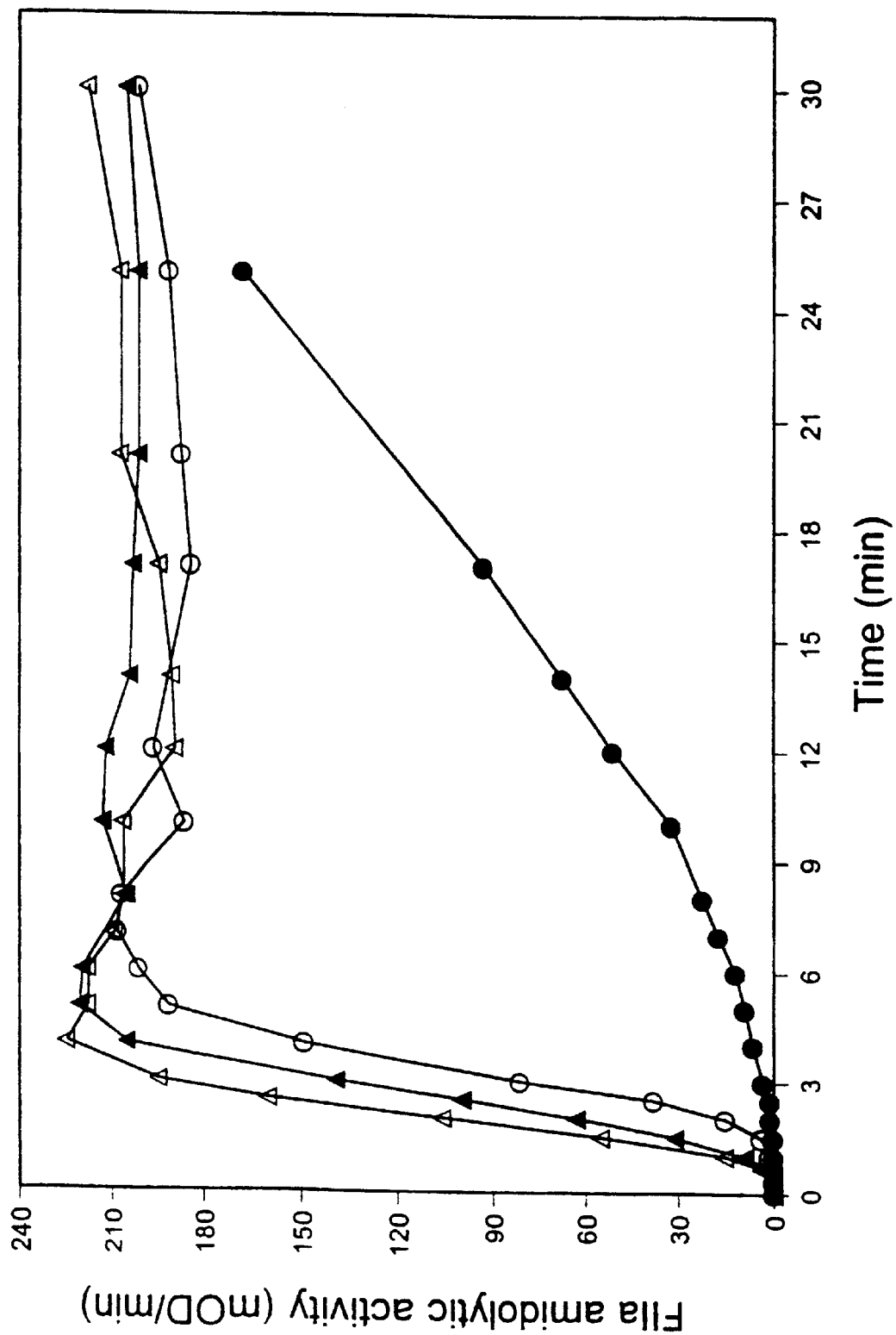

This tissue factor pathway to thrombin experiment was conducted to establish the influence of compounds 1 and 9 on thrombin generation in a reconstituted model of blood coagulation in the presence of TFPI and in the absence of factor VII (FIG. 6).

Tissue factor (0.5 nM) was relipidated into 400 μM PCPS vesicles composed of 75% phosphatidylcholine (PC) and 25% phosphatidylserine (PS). The relipidated tissue factor was incubated with 2.5 pM factor VIIa in HBS (20 mM HEPES, 0.15M NaCl, 2 mM CaCl, pH 7.4) for 20 min at 37° C. to form factor VIIa/tissue factor complex. Other proteins were used at plasma concentrations. 20 nM factor V was added to the factor VIIa/tissue factor complex. The initiation of the reactions was started by the additiuon of a zymogen and inhibitor mixture: 1.4 μM prothrombin. 170 nM factor X, 90 nM factor IX, 2.5 nM TFPI, and 40 μM compounds 1 or 9 (all concentrations final). In the control experiments factor VIII was present and inhibitors were absent. Final concentration of factor VIIa was 1.25 pM, final concentration of tissue factor was 0.25 nM. At selected time points, 5 μl aliquots were removed and quenched into 40 nM EDTA in TBS (20 mM Tris, 0.15M NaCl, pH 7.4) for thrombin amidolytic activity assays employing 200 μM chromogenic substrate Spectrozyme TH.

EXAMPLE 8

Figure 7:
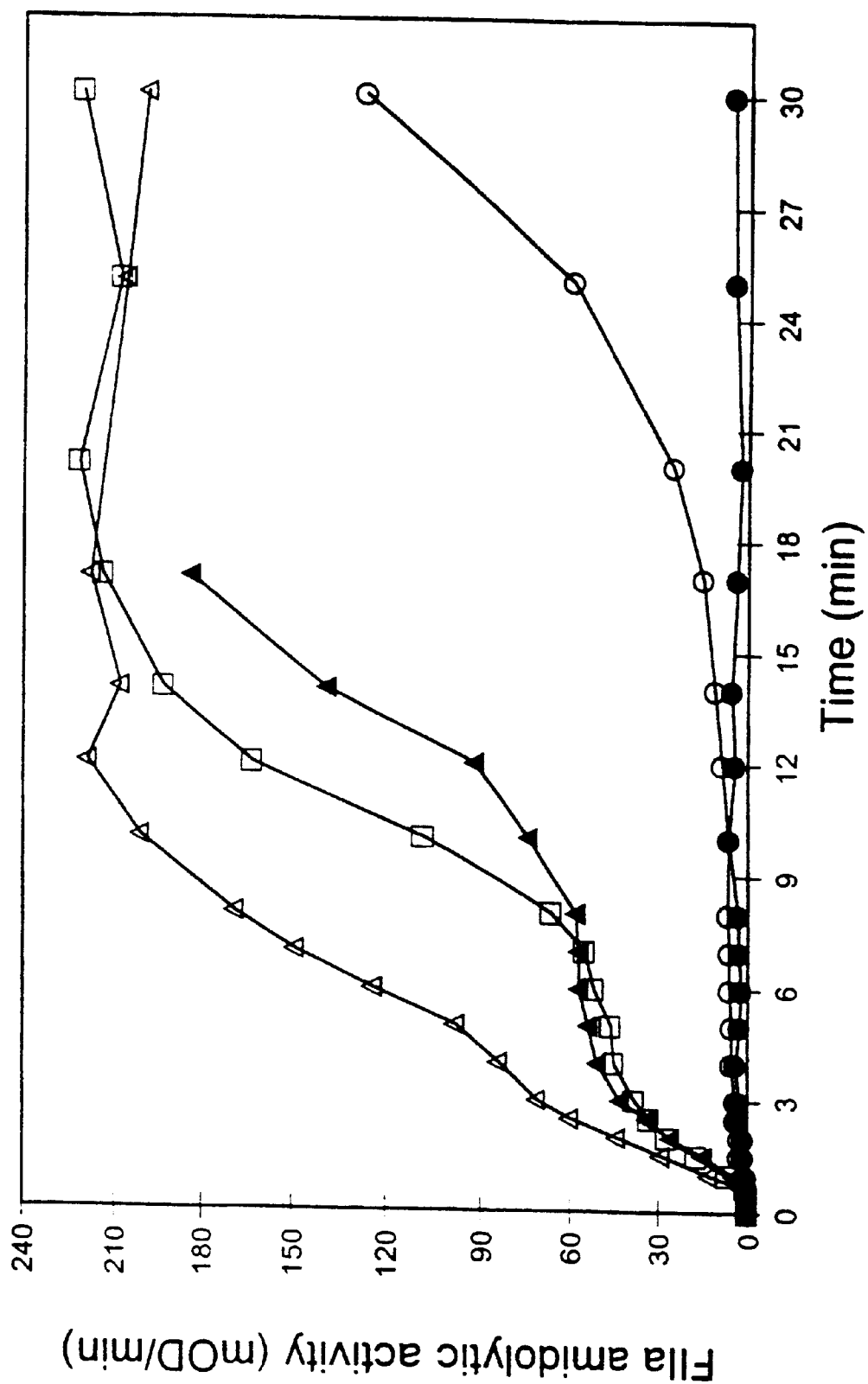

This tissue factor pathway to thrombin experiment was conducted to establish the influence of compounds 1 and 9 on thrombin generation in a reconstituted model of blood coagulation in the presence of APC pathway and TFPI, and in the absence of factor VIII (FIG. 7).

Tissue factor (0.5 nM) was relipidated into 400 μM of PCPS vesicles composed of 75% phosphatidylcholine (PC)

and 25% phosphatidylserine (PS). The relipidated tissue factor was incubated with 2.5 pM factor VIIa in HBS (20 mM HEPES, 0.15M NaCl, 2 mM CaCl, pH 7.4) for 20 min at 37° C. to form factor VIIa/tissue factor complex. Other proteins were used at plasma concentrations. 20 nM factor V and 10 nM thrombomodulin were added to the factor VIIa/tissue factor complex. The initiation of the reaction was started by the addition of a zymogen and inhibitor mixture: 1.4 $\mu$M prothrombin, 170 nM factor X, 90 nM factor X, 70 nM APC, 2.5 nM TFPI, and either 40 $\mu$M compounds 1 or 9, or both of them (20 $\mu$M each) (all concentrations final). In the control experiments factor VIII was present and inhibitors were absent. Final concentration of factor VIIa was 1.25 pM, final concentration of tissue factor was 0.25 nM. At selected time points, 5 $\mu$l aliquots were removed and quenched into 40 mM EDTA in TBS (20 mM Tris, 0.15M NaCl, pH 7.4) for thrombin amidolytic activity assays employing 200 $\mu$M chromogenic substrate Spectrozyme TH. Thrombin concentration was calculated from a standard line.

EXAMPLE 9

Figure 8:
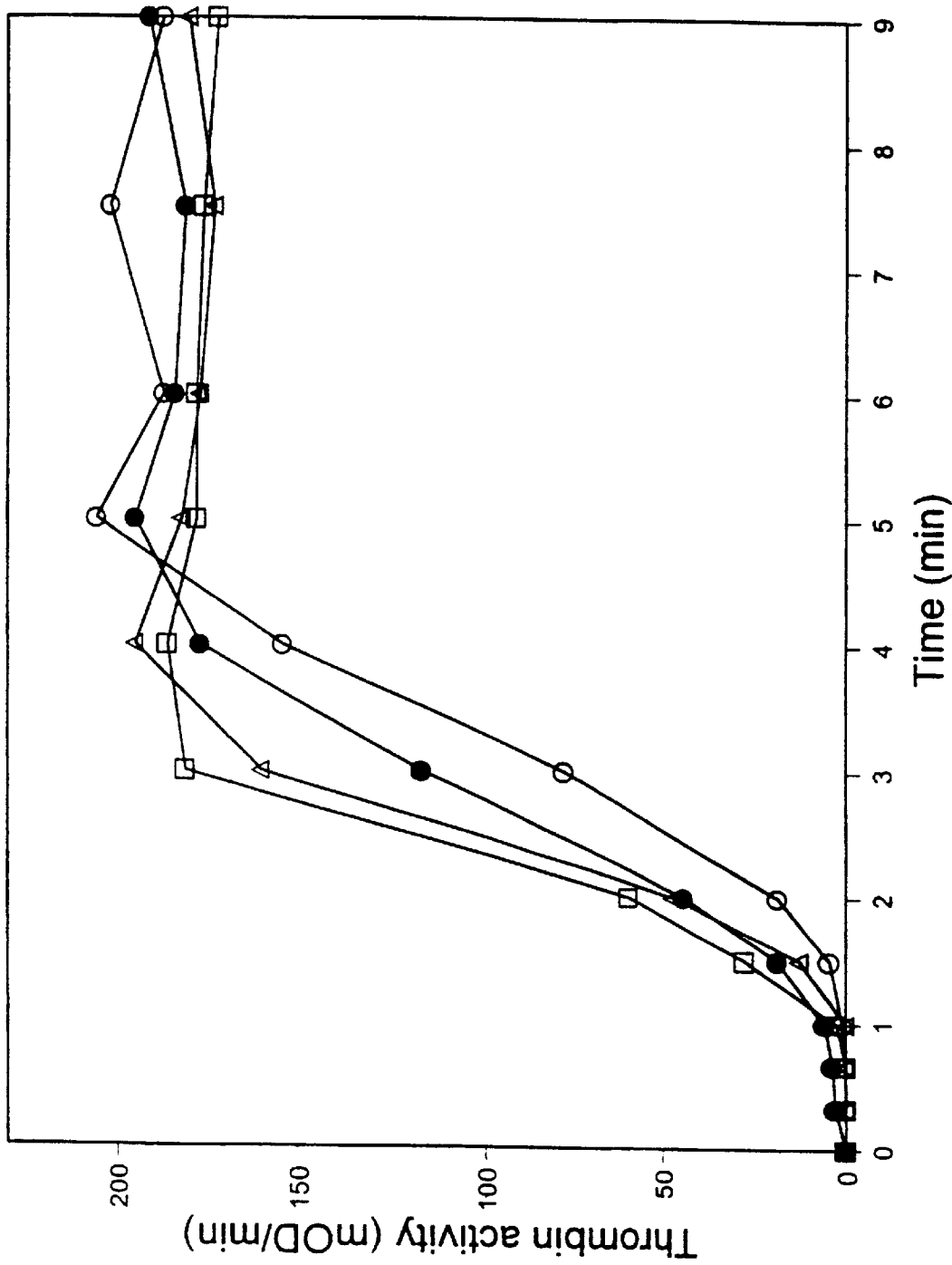

This tissue factor pathway to thrombin experiment was conducted to establish the influence of compounds 1, 9, and 26 on thrombin generation in a reconstituted model of blood coagulation (FIG. 8).

Tissue factor (0.5 nM) was relipidated into 400 $\mu$M PCPS vesicles composed of 75% phosphatidylcholine (PC) and 25% phosphatidylserine (PS). The relipidated tissue factor was incubated with 2.5 pM factor VIIa in HBS (20 mM HEPES, 0.15M NaCl, 2 mM CaCl, pH 7.4) for 20 min at 37° C. to form factor VIIa/tissue factor complex. Other proteins were used at plasma concentrations. 20 nM factor V and 0.7 nM factor VIII were added to the factor VIIa/tissue factor complex. The initiation of the reaction was started by the addition of a zymogen and inhibitor mixture: 1.4 $\mu$M prothrombin, 170 nM factor X, 90 nM factor IX, and 40 $\mu$M compounds 1, 9, or 26 (all concentrations final). In the control experiment inhibitors were absent. Final concentration of factor VIIa was 1.25 pM, final concentration of tissue factor was 0.25 nM. At selected time points, 5 $\mu$l aliquots were removed and quenched into 40 mM EDTA in TBS (20 mM Tris, 0.15M NaCl, pH 7.4) for thrombin amidolytic activity assays employing 200 $\mu$M chromogenic substrate Spectrozyme TH.

The results of the experiment presented in FIG. 2 (Example 3) demonstrate that in the absence of PC (open circles), the explosive phase of thrombin generation appears approximately 2 min after initiation. Protein C pathway prolongs the initiation phase to approximately 10 min and decreases the maximum rate of thrombin generation (filled circles). The presence of compounds 1 or 9 completely compensates for the presence of PC pathway shifting the thrombin generation rate to the higher limit than that in the absence of PC (triangles). This effect is caused by the delay in factor Va and factor VIIIa inactivation by APC, and by the acceleration of coagulation cascade.

Similar results were obtained in the experiment of example 4 (FIG. 3). In the absence of factor VIII (open squares), i.e., in a situation similar to that of hemophilia A, the explosive phase of thrombin generation is delayed by approximately 3 min. In the presence of compounds 1 or 9, however, the absence of factor VIII is completely compensated (diamonds). Moreover, the explosive phase of thrombin generation occurs earlier than in the control experiment where factor VIII is present (filled squares). The maximum rate of thrombin generation in the presence of compound 1 and in the absence of factor VIII (open diamonds) is significantly higher than that in control experiment or in the presence of compound 9. This effect of compound 1 may be caused by higher affinity of this compound for APC than that of compound 9 and, thus, by the more efficient protection of factor Va and factor VIIIa from inactivation by APC.

Among the known in vivo inhibitors of the factor VIIa/tissue factor complex and factor Xa, TFPI appears to be the most efficient. Results of the experiments presented below clearly demonstrate that TFPI may significantly slow down or even stop enzymatic reactions initiated by the factor VIIa/tissue factor complex or factor Xa. Data presented in FIGS. 4 and 5 indicate that in the presence of TFPI, the activity of the factor VIIa/tissue factor complex (FIG. 4, example 5) or factor Xa (FIG. 5, example 6) is decreased to a few percent of that demonstrated in the absence of TFPI. Both compounds tested (#1 and #9) are able to diminish the influence of TFPI on both enzymes, factor Xa and factor VIIa/tissue factor complex in a concentration-dependent manner. They display a similar efficiency in protection from inhibition by TFPI. Thus, the concentration of compound 1 required to restore 50% of the factor VIIa/tissue factor complex amidolytic activity is 10 $\mu$M, whereas the required concentration of compound 9 is 11 $\mu$M. Both compounds are less efficient in the case of factor Xa protection. Thus, the concentration of compound 1 required to restore 50% of factor Xa amidolytic activity is 26 $\mu$M, whereas the concentration of compound 9 required to reach such effect if 26 $\mu$M.

Increasing the complexity of experiments, we tested the ability of compounds 1 and 9 to accelerate thrombin generation in a reconstituted model of the tissue factor pathway to thrombin in the presence of TFPI (example 7, FIG. 6). Results of this experiment demonstrate that TFPI delays the explosive phase of thrombin generation (open circles). Moreover, in the absence of factor VIII, the lag phase of thrombin generation is significantly extended and the maximum rate of reaction is approximately 10-fold lower than in control experiment (filled circles). Compounds 1 and 9 not only compensate for the absence of factor VIII bt allow the reaction to reach explosive thrombin generation phase faster (triangles) than in the control experiment. These data indicate the protection of enzymes and enzymatic complexes occurring in the system from inactivation by TFPI.

In an experiment described in example 8 (FIG. 7) we created a situation which is similar to that occurring in vivo in case of hemophilia A, i.e., the coagulation cascade was initiated in the presence of antagonists of coagulation (TFPI and PC pathway) and in the absence of factor VIII (filled circles). At these conditions thrombin generation is barely detectable and does not reach the explosive phase within 30 min. In the presence of compounds 1 or 9 (triangles) or their equimolar mixture (squares), the absence of factor VIII is completely compensated. The lag phase of reaction is diminished due to the protection of enzymes from TFPI, whereas inhibition of APC causes an increased maximum rate of thrombin generation.

The excessive rate of thrombin generation in the experiments presented in FIGS. 2, 3, 6, 7 when compound 1 or 9 were present lead to the question of whether these compounds are able to increase the thrombin generation rate in the system where inhibitors of coagulation are absent. Thus, the next tissue factor pathway to thrombin experiment was accomplished in the absence of protein C and TFPI. The data shown in FIG. 8 (example 9) clearly demonstrate that compounds 1, 9, and 26 are able to decrease the lag phase of thrombin generation. Compounds 1 and 26 can also increase the maximum rate of prothrombin activation.

Thus, data presented in examples 2–9 clearly demonstrate that compounds presented in this invention are potential procoagulants due to:

1. Inhibition of APC
2. Protection of the factor VIIa/tissue factor complex from TFPI
3. Acceleration of coagulation cascade.

EXAMPLE 10

Blood plasma clotting experiments were conducted to establish the influence of synthesized compounds on plasma clotting time in vitro (Table 3).

100 μl of citrated plasma and 100 μl of HBS in one tube and 100 μl of 25 mM $CaCl_2$ in HBS containing tissue factor relipidated on PCPS and selected synthetic compound (10 mM stock solution in DMSO) in another tube were incubated at 37° C. for 2 min. The contents of both tubes were mixed together, and plasma clotting time was visually established. Final concentrations of reactants were: tissue factor/PCPS 0.625 nM/2.5 μM; synthetic compounds 40 μM. In control experiments synthetic compounds were absent and corresponding amount of DMSO was present.

EXAMPLE 11

Whole blood clotting experiment was conducted to establish the influence of synthesized compounds on blood clotting time in vitro (Table 4).

1 ml of fresh blood was injected into a tube which contained 50 μg/ml of corn trysin inhibitor, 25 pM tissue factor relipidated on 50 nM PCPS, and 20 μM compounds 25–27. Blood clotting time was visually established. In a control experiment compounds were absent and 2 μl of DMSO were present.

---

What is claimed is:

1. A compound of the formula:

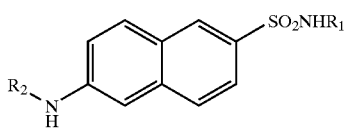

or a salt thereof; wherein $R_1$ is a peptide of the formula

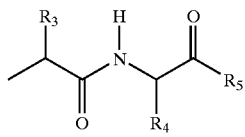

wherein $R_3$ and $R_4$ independently represent free or protected amino acid side chains;

$R_5$ is hydroxy, alkoxy, benzoxy, an amino acid or a peptide residue; and $R_2$ is an amino acid or a peptide residue.

2. A compound according to claim 1, wherein $R_2$ is L- or D-arginine, homoarginine or β-homoarginine.

3. A compound according to claim 1, where $R_2$ is a peptide having L- or D-arginine, homoarginine or β-homoarginine at the carboxy terminus.

4. A compound of the formula:

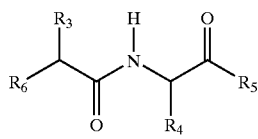

or a salt thereof wherein:

$R_3$ and $R_4$ independently represent free or protected amino acid side chains;

$R_5$ is hydroxy, alkoxy, benzoxy, an amino acid or a peptide residue; and $R_6$ represents a group of the formula:

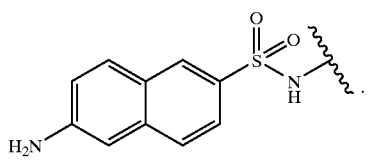

5. A compound of the formula:

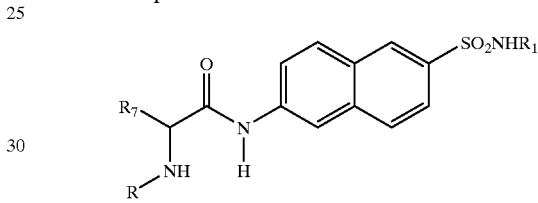

or a salt thereof wherein $R_1$ is a peptide of the formula

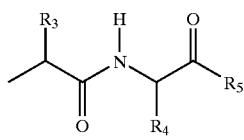

wherein $R_3$ and $R_4$ independently represent free or protected amino acid side chains;

$R_5$ is hydroxy, alkoxy, benzoxy, an amino acid or a peptide residue;

R represents an amino acid or a peptide residue; and $R_7$ represents the side chain of L-arginine, D-arginine, homoarginine or β-homoarginine.

6. A compound of the formula

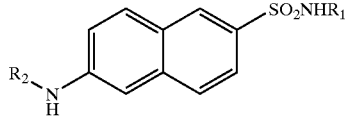

wherein:

$R_2$ is Lys-Lys-Thr-Harg- [SEQ ID NO:35] and $R_1$ is Lys(Z)-Lys(Z)-OBz;

$R_2$ is Boc-Ser-Trp-Arg-Harg- [SEQ ID NO:36] and $R_1$ is -Ser-Glu(OBz);

$R_2$ is Boc-Val-Asp(Me)-Gln-Harg- [SEQ ID NO:37] and $R_1$ is -Glu-Ile-OBz;

R₂ is Boc-Leu-Asp(Me)-Arg-Harg- [SEQ ID NO:38] and R₁ is -Gln-Arg-OEt;

R₂ is Leu-Asp(Me)-Arg-Harg- [SEQ ID NO:39] and R₁ is -Gln-Arg-OEt;

R₂ is Pro-Glu-Leu-Harg- [SEQ ID NO:40] and R₁ is -Asn-Asn-OBz;

R₂ is Harg- and R₁ is -Lys(Z)-Lys(Z)-OBz;

R₂ is Boc-Lys(Boc)-Lys(Boc)-Thr-Harg- [SEQ ID NO:41] and R₁ is -Lys(Z)-Lys(Z)-OBz;

R₂ is Boc-Lys(Boc)-Lys(Boc)-Thr-Harg- [SEQ ID NO:41] and R₁ is -Lys(Boc)-Lys(Z)-OBz;

R₂ is Boc-Lys(Boc)-Lys(Boc)-Thr-Harg- [SEQ ID NO:41] and R₁ is -Lys(Boc)-Lys(Boc)-OMe;

R₂ is Lys-Lys(Z)-Thr-Harg- [SEQ ID NO:42] and R₁ is -Lys(Z)-OBz;

R₂ is Lys(Z)-Lys(Z)-Thr-Harg- [SEQ ID NO:43] and R₁ is -Lys(Z)-OBz;

R₂ is Z-Lys-Lys-Thr-Harg- [SEQ ID NO:44] and R₁ is -Lys(Z)-Lys(Z)-OBz;

R₂ is Z-Lys-Lys-Thr-(-O-Harg)- [SEQ ID NO:45] and R₁ is -Lys(Z)-Lys(Z)-OBz,

R₂ is Z-Lys-Lys-Thr-(D-Arg)- [SEQ ID NO:46] and R₁ is -Lys(Z)-Lys(Z)-OBz;

R₂ is Z-Lys-Lys(Z)-Thr-Harg- [SEQ ID NO:47] and R₁ is -Lys(Z)-Lys(Z)-OBz;

R₂ is Lys(Z)-Lys(Z)-Thr-Harg- [SEQ ID NO:43] and R₁ is -Lys(Z)-Lys(Z)-OBz;

R₂ is Lys-Lys:-Thr-Harg- [SEQ ID NO:35] and R₁ is -Lys-Lys(Z)-OBz;

R₂ is Lys-Lys-Thr-Harg- [SEQ ID NO:35] and R₁ is -Lys-Lys-OMe;

R₂ is H and R₁ is -Lys(Z)-Lys(Z)-OBz;

R₂ is H and R₁ is -Ser-Ser-OBz;

R₂ is H and R₁ is -Glu-Ile-OBz;

R₂ is H and R₁ is -Asn-Asn-OBz;

R₂ is H and R₁ is -Ser-Glu-OBz; or

R₂ is Boc-Lys(Z)-Lys(Z)-Thr-Harg- [SEQ ID NO:48] and R₁ is -Lys(Z)-Lys(Z)-OBz;

where
Harg represents a homo-arginine residue;
Z is benzyloxycarbonyl; and
OBz represents benzyloxy.

7. A compound selected from the group consisting of:

Ile-Glu(OBz)-Pro-Harg-Asn-Ser-Glu-OBz [SEQ ID NO:19];

H₂N-Lys(Z)-Lys(Z)-OBz;

Boc-Lys(Z)-Lys(Z)-Thr-OH;

Boc-Lys(Z)-Lys(Z)-OBz;

Boc-Lyz(Z)-Lys(Z)-OH;

H₂N-Lys(Z)-Lys(Z)-Thr-OH;

Z-Lys(Boc)-Lys(Z)-Thr(Bz)-OH; and

H₂N-Ser-Ser-OBz where
Bz is benzyl;
Harg represents a homo-arginine residue;
Z is benzyloxycarbonyl; and
OBz represents benzyloxy.

8. A compound of the formula:

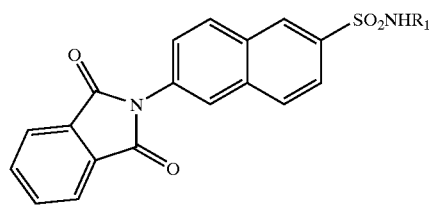

where R₁ is -Lys(Z)-Lys(Z)-Obz where Z is benzyloxycarbonyl and OBZ represents benzyloxy.

* * * * *

SEQUENCE LISTING

<160> NUMBER OF SEQ ID NOS: 48

<210> SEQ ID NO 1
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 1

Lys Lys Thr Arg Asn Pro Lys Lys
1               5

<210> SEQ ID NO 2
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 2

Leu Asp Arg Arg Gly Ile Gln Arg
1               5

<210> SEQ ID NO 3
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 3

Met Ala Thr Arg Lys Met His Asp
1               5

<210> SEQ ID NO 4
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 4

Arg Leu Lys Lys Ser Gln Phe Leu
1               5

```
<210> SEQ ID NO 5
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 5

Pro Gln Leu Arg Met Lys Asn Asn
1               5

<210> SEQ ID NO 6
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 6

Val Asp Gln Arg Gly Asn Gln Ile
1               5

<210> SEQ ID NO 7
<211> LENGTH: 8
<212> TYPE: PRT
<213> ORGANISM: Artificial Sequence
<220> FEATURE:
<223> OTHER INFORMATION: APC natural substrate cleavage site

<400> SEQUENCE: 7

Ile Glu Pro Arg Ser Phe Ser Gln
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN

<400> SEQUENCE: 8

Lys Lys Thr Arg Xaa Lys Lys
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Homoarginine
<220> FEATURE:
<221> NAME/KEY: MISC_FEATURE
<222> LOCATION: (2)..(2)
<223> OTHER INFORMATION: X is ANSN
<220> FEATURE:
<221> NAME/KEY: MISC_FEATURE
<222> LOCATION: (3)..(4)
<223> OTHER INFORMATION: Z protected side chain
```

```
<220> FEATURE:
<221> NAME/KEY: MISC_FEATURE
<222> LOCATION: (4)..(4)
<223> OTHER INFORMATION: OBz protected C-terminus

<400> SEQUENCE: 9

Arg Xaa Lys Lys
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Fmoc protected N-terminus
<220> FEATURE:
<221> NAME/KEY: MISC_FEATURE
<222> LOCATION: (1)..(1)
<223> OTHER INFORMATION: Homoarginine
<220> FEATURE:
<221> NAME/KEY: MISC_FEATURE
<222> LOCATION: (2)..(2)
<223> OTHER INFORMATION: X is ANSN
<220> FEATURE:
<221> NAME/KEY: MISC_FEATURE
<222> LOCATION: (3)..(4)
<223> OTHER INFORMATION: Z protected side chain
<220> FEATURE:
<221> NAME/KEY: MISC_FEATURE
<222> LOCATION: (4)..(4)
<223> OTHER INFORMATION: OBz protected C-terminus

<400> SEQUENCE: 10

Arg Xaa Lys Lys
1

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
<222> LOCATION: (1)..(2)
<223> OTHER INFORMATION: Boc protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 11

Lys Lys Thr Arg Xaa Lys Lys
1               5
```

```
<210> SEQ ID NO 12
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 12

Lys Lys Thr Arg Xaa Lys Lys
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Homoarginine
<220> FEATURE:
<221> NAME/KEY: MISC_FEATURE
<222> LOCATION: (4)..(4)
<223> OTHER INFORMATION: X is ANSN
<220> FEATURE:
<221> NAME/KEY: MISC_FEATURE
<222> LOCATION: (4)..(4)
<223> OTHER INFORMATION: Bz protected C-terminus

<400> SEQUENCE: 13

Val Leu Arg Xaa
1

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: OBz protected side chain
```

```
<220> FEATURE:
<221> NAME/KEY: MISC_FEATURE
<222> LOCATION: (7)..(7)
<223> OTHER INFORMATION: OBz protected C-terminus

<400> SEQUENCE: 14

Ser Trp Arg Arg Xaa Ser Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: OBz protected C-terminus

<400> SEQUENCE: 15

Val Asp Gln Arg Xaa Glu Ile
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MOD_RES
<222> LOCATION: (4)..(4)
<223> OTHER INFORMATION: METHYLATION
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: OEt protected C-terminus

<400> SEQUENCE: 16

Leu Asp Arg Arg Xaa Gln Arg
1               5
```

```
<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: misc_feature
<222> LOCATION: (4)..(4)
<223> OTHER INFORMATION: Homoarginine
<220> FEATURE:
<221> NAME/KEY: misc_feature
<222> LOCATION: (5)..(5)
<223> OTHER INFORMATION: X is ANSN
<220> FEATURE:
<221> NAME/KEY: misc_feature
<222> LOCATION: (7)..(7)
<223> OTHER INFORMATION: OEt protected C-terminus

<400> SEQUENCE: 17

Leu Asp Arg Arg Xaa Gln Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: OBz protected C-terminus

<400> SEQUENCE: 18

Pro Glu Leu Arg Xaa Asn Asn
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: OBz protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (6)..(6)
<223> OTHER INFORMATION: OBz protected C-terminus

<400> SEQUENCE: 19

Ile Glu Pro Arg Asn Ser Glu
1               5
```

```
<210> SEQ ID NO 20
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
<222> LOCATION: (1)..(2)
<223> OTHER INFORMATION: Boc protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(6)
<223> OTHER INFORMATION: Boc protected side chain
<220> FEATURE:
<221> NAME/KEY: MISC_FEATURE
<222> LOCATION: (7)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 20

Lys Lys Thr Arg Xaa Lys Lys
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
<222> LOCATION: (1)..(2)
<223> OTHER INFORMATION: Boc protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Boc protected side chain
<220> FEATURE:
<221> NAME/KEY: MISC_FEATURE
<222> LOCATION: (7)..(7)
<223> OTHER INFORMATION: OMe protected C-terminus

<400> SEQUENCE: 21

Lys Lys Thr Arg Xaa Lys Lys
1               5
```

```
<210> SEQ ID NO 22
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (5)..(5)
<223> OTHER INFORMATION: Bz protected c-terminus

<400> SEQUENCE: 22

Lys Lys Thr Arg Xaa
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(6)
<223> OTHER INFORMATION: Z protected side chain
<220> FEATURE:
<221> NAME/KEY: MISC_FEATURE
<222> LOCATION: (6)..(6)
<223> OTHER INFORMATION: OBz protected C-terminus

<400> SEQUENCE: 23

Lys Lys Thr Arg Xaa Lys
1               5

<210> SEQ ID NO 24
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(6)
```

```
<223> OTHER INFORMATION: Z protected side chain
<220> FEATURE:
<221> NAME/KEY: MISC_FEATURE
<222> LOCATION: (6)..(6)
<223> OTHER INFORMATION: OBz protected C-terminus

<400> SEQUENCE: 24

Lys Lys Thr Arg Xaa Lys
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 25

Lys Lys Thr Arg Xaa Lys Lys
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (4)..(4)
<223> OTHER INFORMATION: beta-Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 26

Lys Lys Thr Arg Xaa Lys Lys
1               5
```

```
<210> SEQ ID NO 27
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (4)..(4)
<223> OTHER INFORMATION: D-Arginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 27

Lys Lys Thr Arg Xaa Lys Lys
1               5

<210> SEQ ID NO 28
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (2)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 28

Lys Lys Thr Arg Xaa Lys Lys
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
```

```
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 29

Lys Lys Thr Arg Xaa Lys Lys
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (3)..(3)
<223> OTHER INFORMATION: OBz protected side chain
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 30

Lys Lys Thr Arg Xaa Lys Lys
1               5

<210> SEQ ID NO 31
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: Z protected side chain
```

```
<220> FEATURE:
<221> NAME/KEY: MISC_FEATURE
<222> LOCATION: (7)..(7)
<223> OTHER INFORMATION: OBz protected C-terminus

<400> SEQUENCE: 31

Lys Lys Thr Arg Xaa Lys Lys
1               5

<210> SEQ ID NO 32
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: OMe protected C-terminus

<400> SEQUENCE: 32

Lys Lys Thr Arg Xaa Lys Lys
1               5

<210> SEQ ID NO 33
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (7)..(7)
<223> OTHER INFORMATION: OBz protected C-terminus

<400> SEQUENCE: 33

Lys Lys Thr Arg Xaa Lys Lys
1               5

<210> SEQ ID NO 34
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
<222> LOCATION: (1)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine
```

```
<220> FEATURE:
<221> NAME/KEY: MISC_FEATURE
<222> LOCATION: (5)..(5)
<223> OTHER INFORMATION: X is ANSN
<220> FEATURE:
<221> NAME/KEY: MISC_FEATURE
<222> LOCATION: (6)..(7)
<223> OTHER INFORMATION: Z protected side chain
<220> FEATURE:
<221> NAME/KEY: MISC_FEATURE
<222> LOCATION: (7)..(7)
<223> OTHER INFORMATION: OBz protected C-terminus

<400> SEQUENCE: 34

Lys Lys Thr Arg Xaa Lys Lys
1               5

<210> SEQ ID NO 35
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine

<400> SEQUENCE: 35

Lys Lys Thr Arg
1

<210> SEQ ID NO 36
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
<222> LOCATION: (4)..(1)
<223> OTHER INFORMATION: Homoarginine

<400> SEQUENCE: 36

Ser Trp Arg Arg
1

<210> SEQ ID NO 37
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MOD_RES
<222> LOCATION: (1)..(1)
<223> OTHER INFORMATION: METHYLATION
<220> FEATURE:
<221> NAME/KEY: MISC_FEATURE
<222> LOCATION: (4)..(4)
<223> OTHER INFORMATION: Homoarginine
```

<400> SEQUENCE: 37

Val Asp Gln Arg
1

<210> SEQ ID NO 38
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (4)..(4)
<223> OTHER INFORMATION: Homoarginine

<400> SEQUENCE: 38

Leu Asp Arg Arg
1

<210> SEQ ID NO 39
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: METHYLATION
<220> FEATURE:
<221> NAME/KEY: MISC_FEATURE
<222> LOCATION: (4)..(4)
<223> OTHER INFORMATION: Homoarginine

<400> SEQUENCE: 39

Leu Asp Arg Arg
1

<210> SEQ ID NO 40
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Homoarginine

<400> SEQUENCE: 40

Pro Glu Leu Arg
1

<210> SEQ ID NO 41
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus

```
<220> FEATURE:
<221> NAME/KEY: MISC_FEATURE
<222> LOCATION: (1)..(2)
<223> OTHER INFORMATION: Boc protected side chain
<220> FEATURE:
<221> NAME/KEY: MISC_FEATURE
<222> LOCATION: (4)..(4)
<223> OTHER INFORMATION: Homoarginine

<400> SEQUENCE: 41

Lys Lys Thr Arg
1

<210> SEQ ID NO 42
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine

<400> SEQUENCE: 42

Lys Lys Thr Arg
1

<210> SEQ ID NO 43
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine

<400> SEQUENCE: 43

Lys Lys Thr Arg
1

<210> SEQ ID NO 44
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (4)..(4)
<223> OTHER INFORMATION: Homoarginine

<400> SEQUENCE: 44

Lys Lys Thr Arg
1
```

```
<210> SEQ ID NO 45
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (4)..(4)
<223> OTHER INFORMATION: beta-Homoarginine

<400> SEQUENCE: 45

Lys Lys Thr Arg
1

<210> SEQ ID NO 46
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (4)..(4)
<223> OTHER INFORMATION: D-Arginine

<400> SEQUENCE: 46

Lys Lys Thr Arg
1

<210> SEQ ID NO 47
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Z protected N-terminus
<220> FEATURE:
<221> NAME/KEY: MISC_FEATURE
<222> LOCATION: (2)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine

<400> SEQUENCE: 47

Lys Lys Thr Arg
1

<210> SEQ ID NO 48
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Boc protected N-terminus
<220> FEATURE:
<221> NAME/KEY: MISC_FEATURE
```

```
<222> LOCATION: (1)..(2)
<223> OTHER INFORMATION: Z protected side chain
<220> FEATURE:
<221> NAME/KEY: MISC_FEATURE
<222> LOCATION: (4)..(4)
<223> OTHER INFORMATION: Homoarginine

<400> SEQUENCE: 48

Lys Lys Thr Arg
1
```